United States Patent [19]
Sicurelli et al.

[11] Patent Number: 6,024,565
[45] Date of Patent: Feb. 15, 2000

[54] ENDODONTIC MEASURING SYSTEM

[76] Inventors: Robert Sicurelli, 210 Cir. Rd., Muttontown, N.Y. 11791; Samuel Mayrs, 415 Bay Ridge Pkwy ., Brooklyn, N.Y. 11209

[21] Appl. No.: 09/178,930

[22] Filed: Oct. 26, 1998

[51] Int. Cl.⁷ ..................................................... A61C 5/02
[52] U.S. Cl. ........................................... 433/102; 433/224
[58] Field of Search ............................. 433/72, 75, 102, 433/224

[56] References Cited

U.S. PATENT DOCUMENTS

| | | | |
|---|---|---|---|
| 1,366,877 | 1/1921 | Craig | 433/75 |
| 3,330,040 | 7/1967 | Kahn | 433/72 |
| 3,916,529 | 11/1975 | Mousseau | 433/72 |
| 4,878,842 | 11/1989 | Malcmacher et al. | 433/72 |
| 5,423,677 | 6/1995 | Brattesani | 433/72 |
| 5,605,460 | 2/1997 | Heath et al. | 433/102 |
| 5,685,713 | 11/1997 | Bergstrom et al. | 433/72 |

*Primary Examiner*—Todd E. Manahan
*Attorney, Agent, or Firm*—Alfred M. Walker

[57] ABSTRACT

An endodontic measuring kit includes a plurality of user selectable elongated cylindrical diameter measuring rods having graded diameters known to the user for insertion as probes into an endodontic canal wherein the diameter of the natural lower root tip aperture and length of the tooth canal from apical to coronal end are to be determined. The kit also has a plurality of user selectable elongated tapered rods having graded diameters, wherein the tapered rods each have a top cylindrical portion with optional length measurement markings thereon for observing too the depth from the upper coronal crown end to the lower root apical tip aperture. The tapered rods have a tapered bottom end extending from the top cylindrical portion, and the tapered bottom end has a visual indicator for indicating contact made between the tapered bottom end and the natural contour of a lower endodontic root tip aperture whose diameter and whose length of the tooth canal from apical to coronal end are being determined, prior to endodontic root canal treatment.

12 Claims, 5 Drawing Sheets

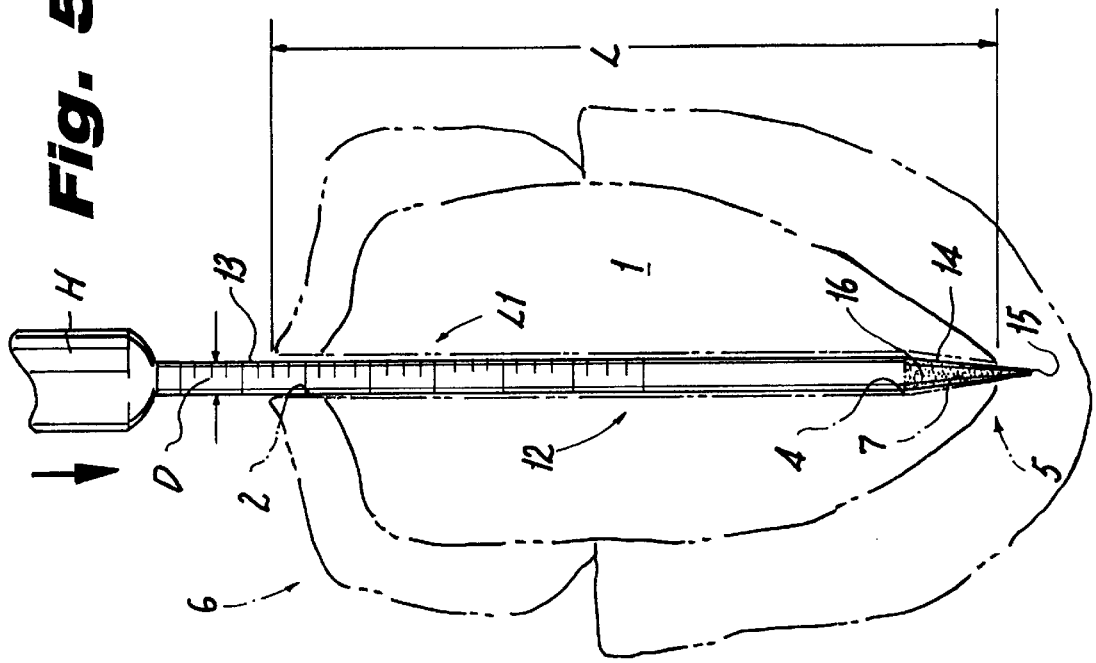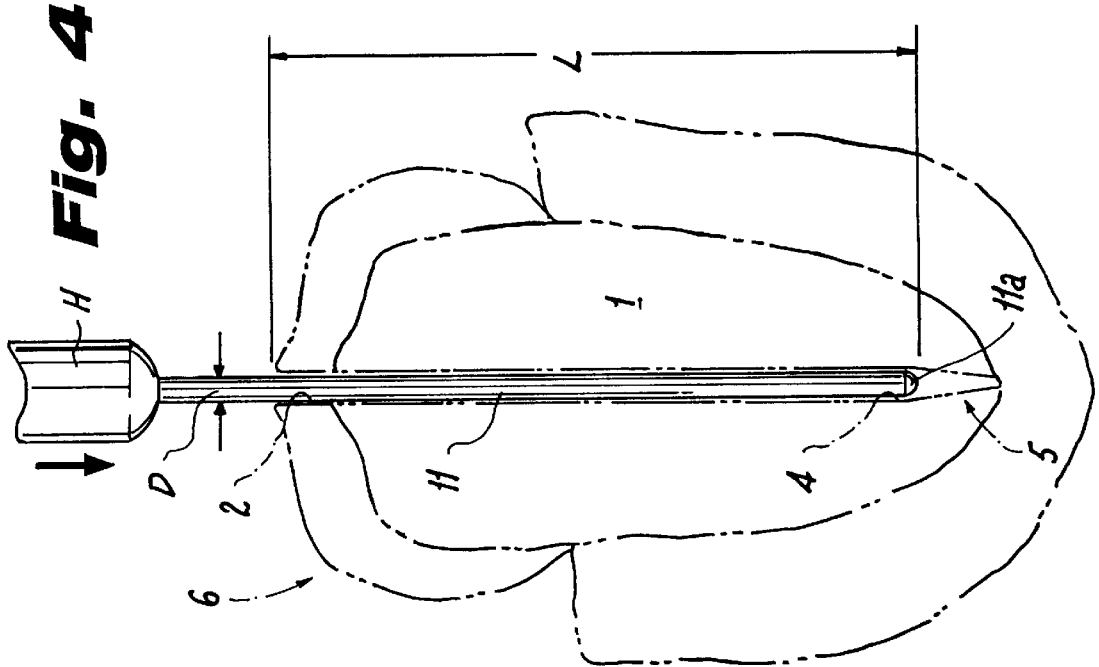

ENDODONTIC MEASURING SYSTEM

FIELD OF THE INVENTION

The present invention relates to measuring apical to coronal depth in a tooth canal in preparation for endodontic treatment.

BACKGROUND OF THE INVENTION

In endodontic treatment, precise measurement control is one of the basic tenants. Canal length is determined by several techniques, the most common being the interpolation of an X-ray of the tooth with an endodontic instrument of known length in place. Another technique involves the use of electrical measuring devices. The endodontic literature has numerous studies that show the reliability of these techniques to be at best 95%.

This limited reliability creates the possibility that the dental practitioner may be misinformed about the exact length of the canal. Current techniques of endodontic treatment strive to have the narrowest point of the canal preparation to be at the apical terminus. This is referred to as the apical constriction. However, as current canal length determination technology provides a less than ideal margin of error. A means of exact determination of the location of the constriction would be a great aid.

OBJECTS OF THE INVENTION

It is therefore an object of the present invention to provide an endodontic measuring kit, which accurately measures the length of a tooth canal to be endodontically treated.

It is also an object of the present invention to provide a measuring system with a plurality of user selectable elongated measuring rods having graded diameters known to the user for insertion as probes into an endodontic canal wherein the diameter and length of the natural lower root tip aperture and length of the tooth canal from apical to coronal end can be determined.

It is yet another object to provide a set of measuring instruments with a set of user selectable elongated tapered rods having graded diameters, for observing tooth depth from crown to lower root tip aperture.

It is yet another object of the present invention to provide sets of measuring instruments with visually ascertainable contact indicating means to ascertain the location of the lower end of the canal to be treated.

It is a further object of the present invention to provide either straight or flexible measuring posts for arcuate determination of the diameter of an endodontic lower root tip aperture and the overall tooth depth from crown to said lower root tip aperture.

It is yet another object of the present invention to provide accurate instrument contact indicating members.

It is yet another object of the present invention to provide an automated electrical signal detection means for detecting the length of a tooth canal with a signal variable according to the place of contact and a signal receiving and signal display for visual display of the location of the bottom end of the tooth canal at which contact has been made.

It is also an object of the present invention to improve over the disadvantages of the Prior Art.

SUMMARY OF THE INVENTION

In keeping with these objects and others which may become apparent, the proposed technique of the present invention involves the use of two sets of calibrated instruments to achieve an exact working length determination. After taking a working length determination by any acceptable technique, the canal is instrumented to remove the organic contents.

The first set of instruments includes parallel sided probes in the standard endodontic sizes (i.e. 10, 20, 30 . . .) but with no taper. These instruments have a continuous diameter for their entire working length. The operator determines the largest sized instrument that will freely pass through the apex of the canal. Preferably each instrument is rounded in a dome at its leading edge.

The second set of instruments includes tapered instruments. From the second set of tapered instruments the operator chooses a device with a tip of the same size diameter as the appropriate parallel-sided instrument from the first set. However, these tapered instruments differ in two significant ways. Firstly, each of these instruments has a taper of either 0.01, 0.03, 0.05, 0.07, 0.09, and 0.11. For purpose of explanation, a 0.03 taper refers to an increase of 0.03 mm in diameter of every 1 mm movement up the shaft of the instrument. These tapers correspond to the current availability of endodontic instruments in tapers of 0.02, 0.04, 0.06, 0.08, 0.10, and 0.12. The operator chooses the instrument with the largest taper that is less than the largest taper used to prepare the apex of the tooth.

Additionally these tapered instruments have a pressure sensitive surface, to indicate when the tip or side of the tapered instrument has physically contacted the natural opening at the bottom apical end of the tooth root to be treated.

When the tapered pressure sensitive instrument is placed into the canal the operator knows that its tapered tip freely passes through the end of the tooth's canal preparation. As it passes beyond the apex of the bottom apical end of the tooth canal, the instrument's increasingly sized taper makes contact with the narrowest point of the preparation, namely, at the aforesaid opening at the bottom of the canal. The instrument's downward progress is ended when the operator feels some binding occurring when the side of the tapered instrument contacts the circumference of the opening. A standard endodontic measuring stop is used to provide measurement control. Once the tapered instrument is withdrawn upward and removed from the tooth canal, the pressure sensitive indicator component, such as a medical grade dye or other visual indicator, can be interpreted to provide an exact length of the canal, since the lower end of the canal is indicated by the mark left by the pressure sensitive indicator component and the upper end at the top of the tooth canal is visually observed at the same time. The length is then the determined distance between the lower and upper ends of the canal.

Optionally, instead of medical grade dye, the pressure sensitive component may be an electronic part inside the probe that detects compression on the probe upon contact with the circumferential edge of the opening at the bottom of the canal. It may also be a pressure sensitive plastic that changes color. This may be a pressure coating dye that wipes off and leaves a visually ascertainable mark on the tapered instrument.

The visually ascertainable mark may also be created by heat softening or chemical softening of the tapered rod with a moldable material, thus producing a model of the canal for use in sealing the canal with gutta percha. Heat softening plasticizes gutta percha on the tapered portion of the rod, so that it can create an image of the tooth canal. Chemical softening also creates such images. Chemical solvents which plasticize gutta percha include chloroform, halothane and eucalyptol.

When the tooth canals are twisted and/or arcuate, the instruments may be made of a flexible plastic or a flexible metal to negotiate curves of the canal. In this way, either a straight linear length of the canal can be measured, or an arcuate tangential arc length of the canal can be measured.

With this information in hand the dentist is better equipped to deal with providing a proper endodontic filling.

DESCRIPTION OF THE DRAWINGS

The present invention can best be described in conjunction with the accompanying drawings, in which:

FIG. 4 is a side elevational view showing the insertion of one parallel sided instrument into a tooth canal, from the set of parallel side instruments, as in FIGS. 1 and 2 herein;

FIG. 5 is a side elevational view, showing the insertion of a tapered instrument into a tooth canal, from the set of tapered instruments, as in FIGS. 1 and 3 herein;

DETAILED DESCRIPTION OF THE PREFERRED EMBODIMENTS

Figure 1:
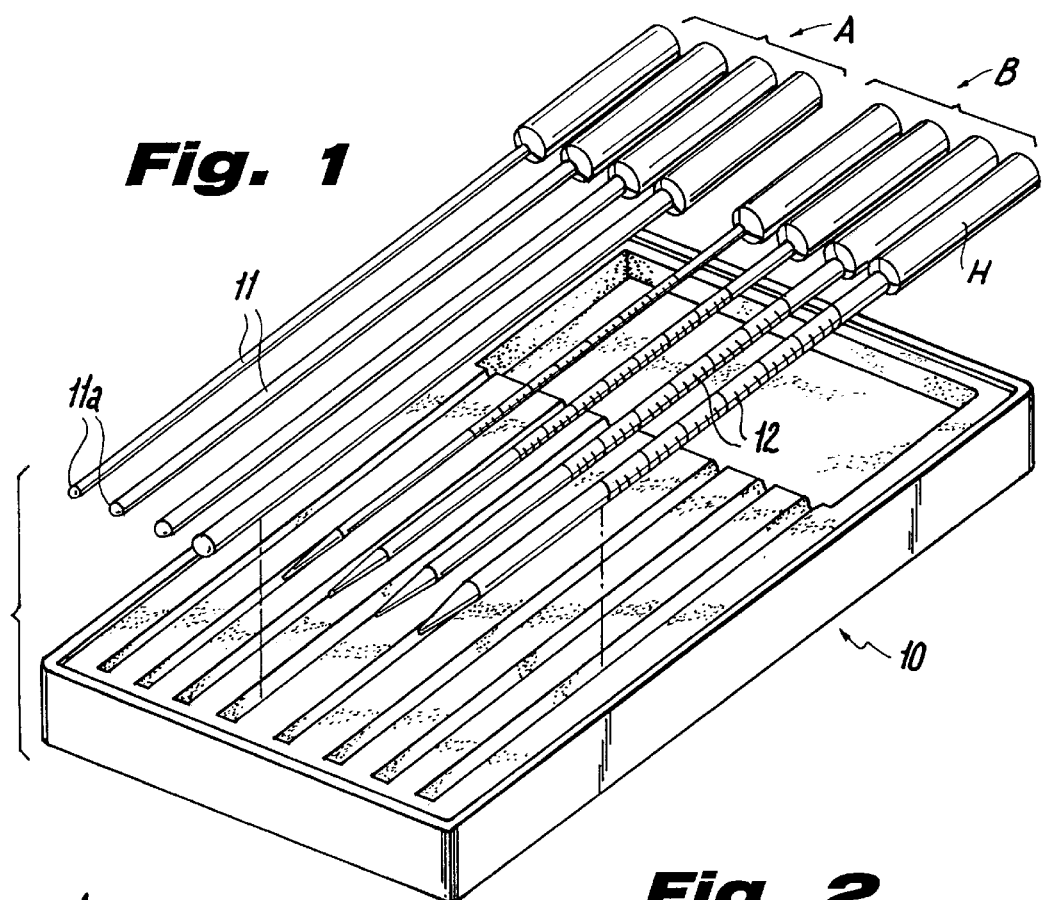
FIG. 1 is an exploded perspective view of the endodontic measuring system of the present invention, having a set of parallel sided instruments and a set of tapered instruments.
Figure 2:
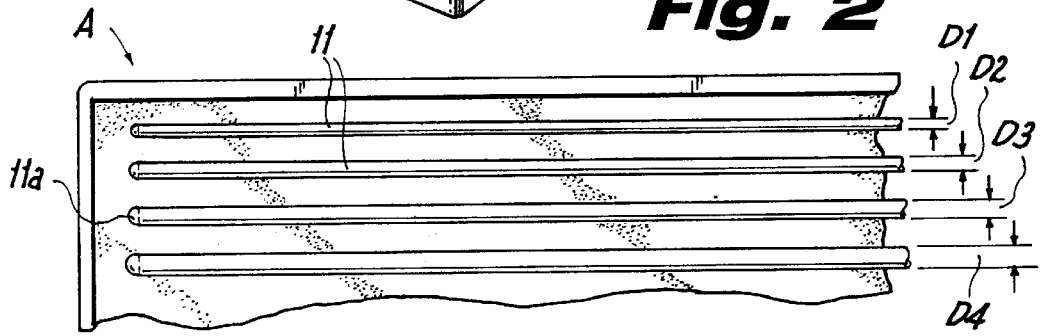
FIG. 2 is a top plan view of the set of parallel sided measuring instruments, as in FIG. 1.
Figure 3:
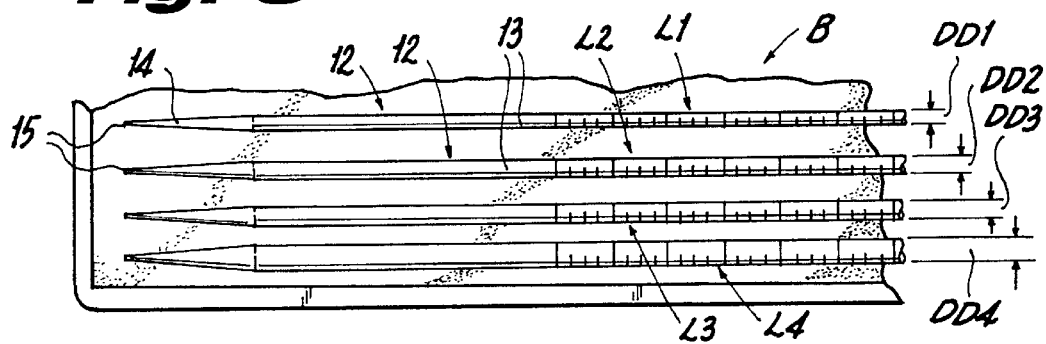
FIG. 3 is a top plan view of the set of tapered measuring instruments, as in FIG. 1.
Figure 7:
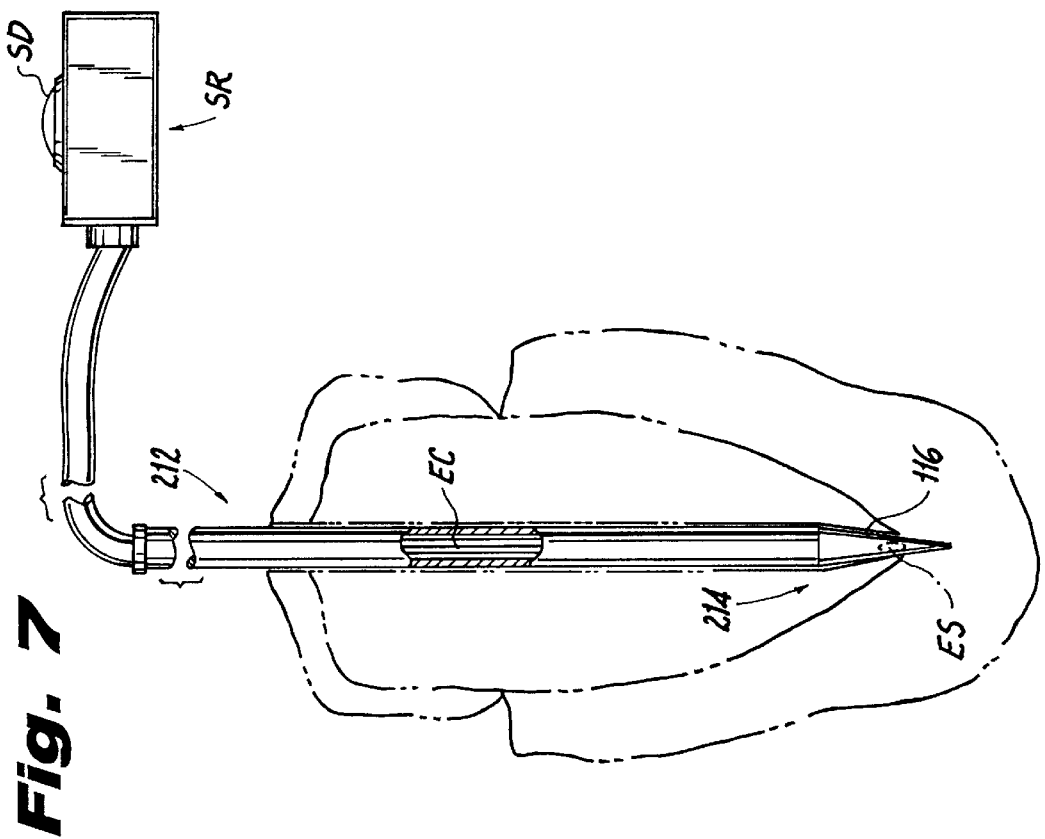
FIG. 7 is a side elevational view of an alternate embodiment for an electrical endodontic tooth canal measuring system.

As shown in the Drawing Figures, the present invention is an endodontic measuring kit 10, including two sets A,B of measuring posts 11, 12.

The first set "A" of rods 11 includes a plurality of user selectable elongated cylindrical diameter measuring rods 11 having graded diameters "D1", "D2", "D3", "D4", etc., known to the user for insertion as probes into an endodontic canal 2 of a tooth 1, wherein the diameter "D" of the natural lower root tip aperture 4 and length L of the tooth canal from lower apical end 5 to upper coronal end 6 are to be determined, as in FIG. 4 herein. Rods 11 may optionally have a rounded, domed leading edge.

The second set "B" of rods 12 includes a plurality of user selectable elongated tapered rods 12 having graded diameters "DD1", "DD2", "DD3", "DD4", etc.

Each tapered post 12 has a top longitudinally extending portion 13, preferably cylindrical, that may optionally have length measurement markings L1, L2, L3, etc., thereon for observing tooth depth "L" from coronal crown end 6 to lower apical root tip end 5 having tip aperture 4 thereof, as in FIG. 4 herein. However, unmarked instruments can also be used, wherein the measurements are separately determined by an accessory measuring ruler with length measurements thereon.

Tapered rods 12 each have a tapered bottom end portion 14 extending from a lower end of top cylindrical portion 13 to lower apex tip 15. Tapered bottom end 14 includes visual indicating contact means 16 to indicate contact made between apex tip 15 of tapered bottom end 14 and the natural circumferential contour edge 7 of a lower endodontic root tip aperture 4 of tooth canal 2. Diameter "D" of aperture "A" and length L of the tooth canal, from lower apical end 5 to upper coronal end 6, can be then determined.

Figure 9:
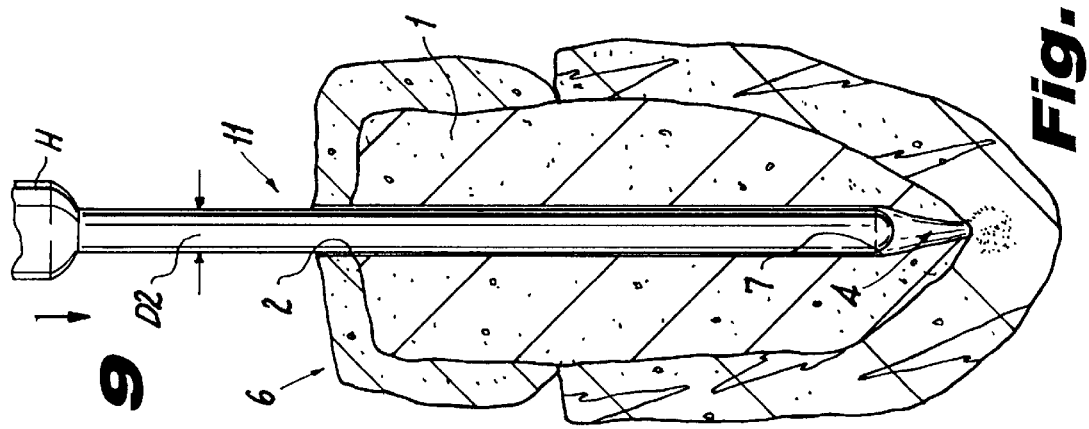
Figure 10:
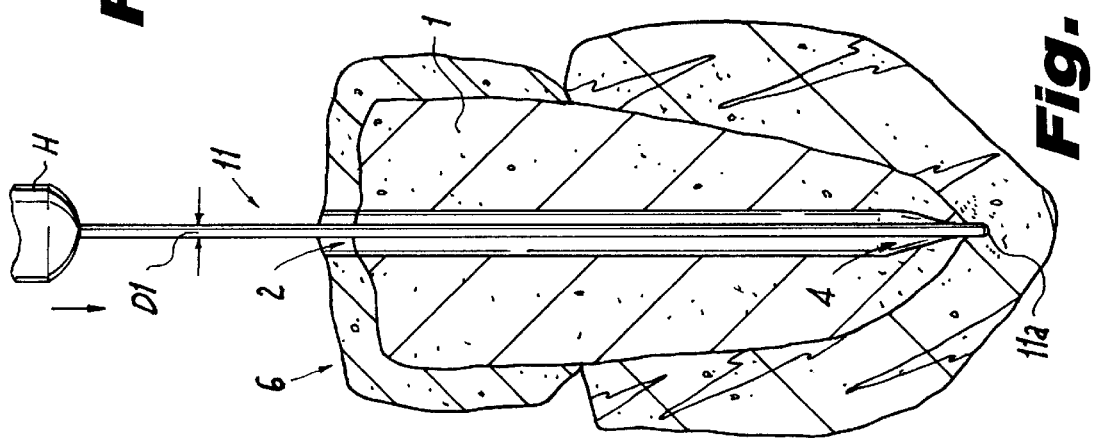
Figure 11:
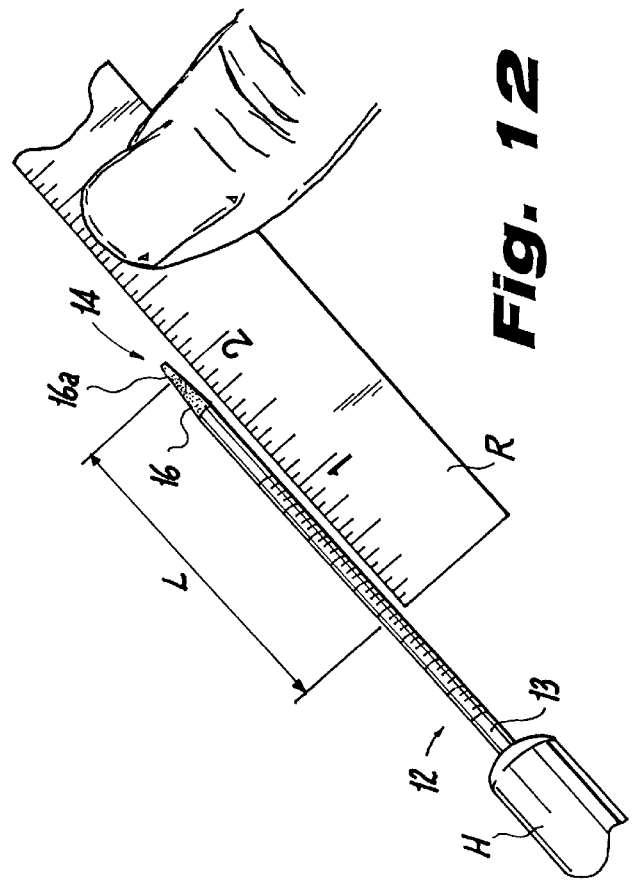
Figure 12:
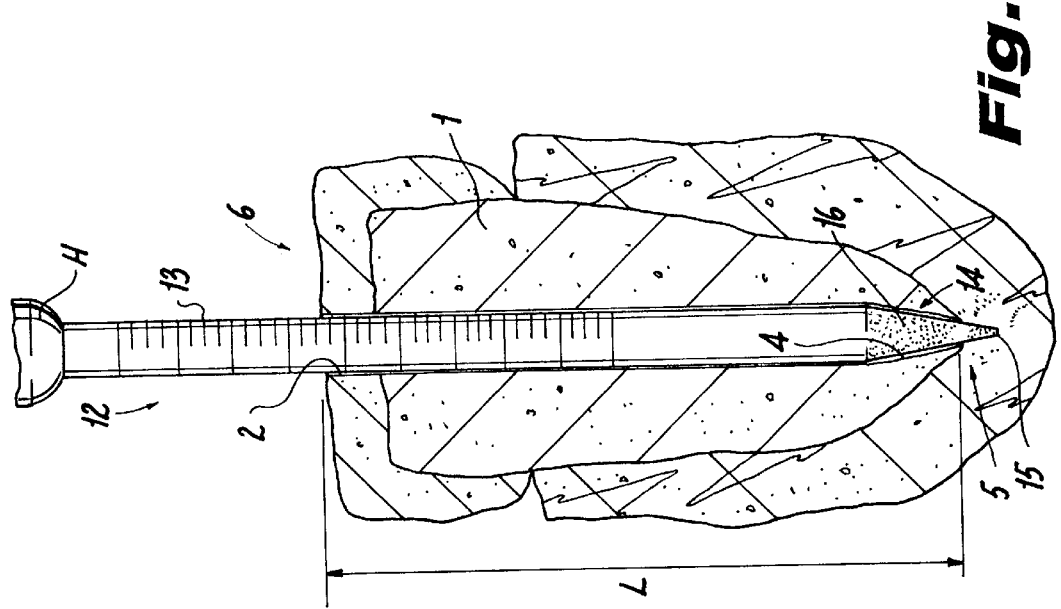

Indicating contact means 16 can be either a pressure sensing means or a visual indication means. For example, indicating contact means 16 may be a pressure sensitive medical grade coating such as a dye, upon tapered bottom end 14, of tapered rod 12, wherein coating 11 of visual indicating means 16 develops a visual indication at the place of contact of tapered bottom end 14 of tapered rod 12 with the natural circumferential contour edge 7, as shown in FIG. 9 herein, of the lower endodontic root tip aperture 4 of canal 2.

Figure 6:
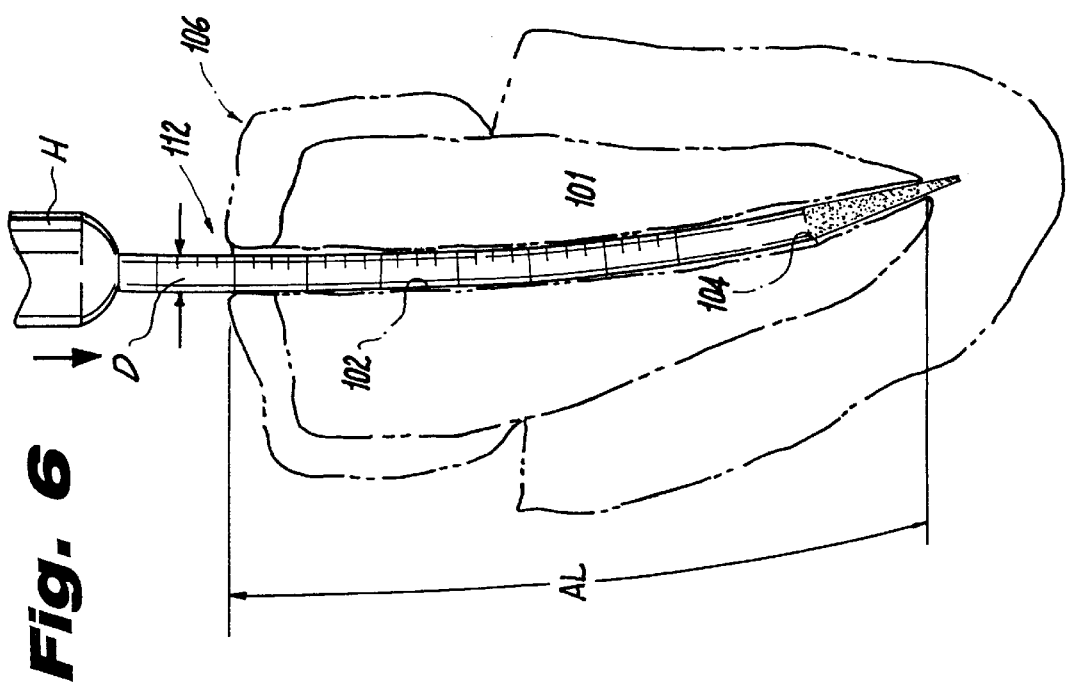
FIG. 6 is a side elevational view of an alternate embodiment for a flexible tapered instrument for insertion into an arcuate canal of a tooth.
Figure 8:
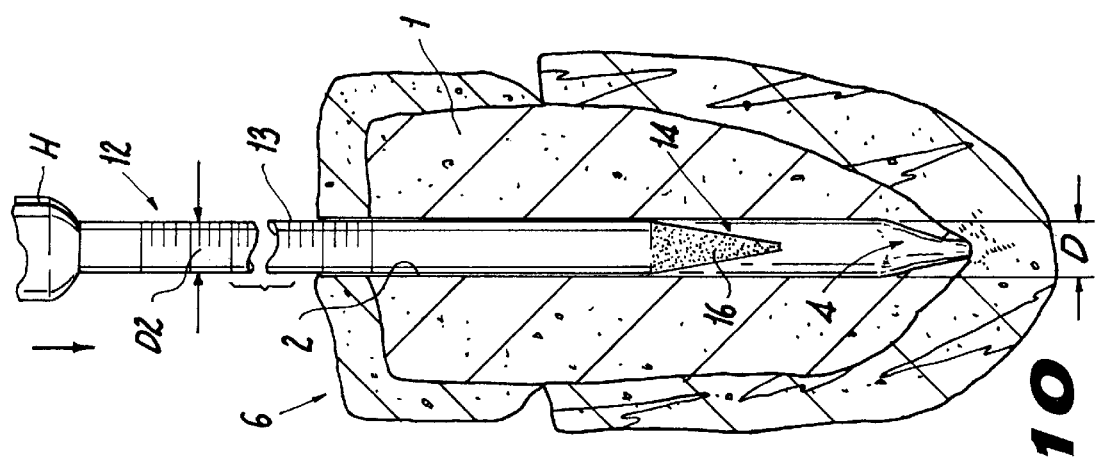
FIGS. 8, 9, 10, 11, 12 show the steps of the method of measuring an endodontic tooth canal, as in the present invention.

As shown in FIG. 6, if canal 2 of tooth 1 is twisted and/or arcuate, flexible cylindrical rods 112 may be provided for arcuate determination of the arc length "AL" of overall tooth depth from upper coronal crown end 106 to lower root tip aperture 104 of canal 102 of tooth 101.

In another embodiment, tapered rod contact indicating means 116 may include an electric circuit EC and electric pressure sensitive switch ES capable of generating a signal variable according to the place of contact of indicating means 116 upon said tapered bottom end 214 of tapered rod 212 and signal receiving SR and signal display means SD for visual display of the place upon tapered bottom end 214 of tapered rod 212 at which contact has been made.

OPERATION OF THE INVENTION

As shown in FIGS. 8, 9, 10, 11 and 12 herein, in endodontic dentistry, the present invention includes a method of measuring the diameter "D" of a lower endodontic root tip aperture 4 and measuring overall tooth depth "L" from upper coronal crown end 6 to lower root apical tip end.

First, into a tooth canal 2 of tooth 1, which canal 2 is open at the upper crown coronal end 6, the user selects and inserts as a probe a parallel sided cylindrical diameter measuring rod 11 of a small, known diameter "D1" into canal 2 of tooth 1 and through natural lower root tip aperture 4.

The user then removes the diameter measuring rod 11 of small, known diameter "D1" and inserts a different cylindrical measuring rod 11 having a known, incrementally larger diameter "D2" as a probe into canal 2 of tooth 1 and also through the natural lower root tip aperture 4.

The user determines the diameter "D" of the natural aperture 4 of the lower tip of a selected tooth root canal 2 by repeating the step of inserting a cylindrical rod 11 with successively larger diameter cylindrical measuring rods 11 until an appropriate sized cylindrical measuring rod 11 encounters contact resistance when the user attempts to insert measuring rod 11 into the natural lower root tip aperture 4 and measuring rod 11 makes contact with circumferential contour edge 7 thereat.

Then the user notes the diameter "D1", "D2", "D3", "D4", etc., of the first cylindrical measuring rod that encounters contact resistance at the natural lower root tip aperture 4 and then removes measuring rod 11.

After that removal of rod 11, the user inserts into canal 2 of tooth 1 and then into root tip aperture 6 a selected tapered-bottom cylindrical measuring rod 12 wherein tapered bottom-cylindrical rod 12 has contact indicating means 16 on tapered-bottom end 14. At that point, tapered-bottom measuring rod 12 has a known diameter "D1", "D2" "D3", "D4", etc., matching diameter "D" of natural lower root tip aperture 4. Furthermore, tapered-bottom measuring rod 12 may have sequential length markings on its upper cylindrical portion 13. If not, a conventional ruler with length measuring markings is placed adjacent to upper cylindrial portion 13.

With this information, the user determines the coronal crown to lower root tip depth L for the diameter-determined selected lower apical root tip end 5 by noting the length markings adjacent to the upper tooth coronal crown end 6 on the tapered-bottom measuring rod 12 when its tapered-bottom portion 13 is in contact with the natural aperture 4 of a selected lower root tip 5.

The user the withdraws tapered-bottom measuring rod 12 from canal 2 of tooth 1, for which depth L is being determined.

The user observes and notes the place on tapered bottom portion 14, where contact indicating means 16 shows a visible contact indication, such as a visually perceptible mark, and measures and notes the distance between the visible contact indication and the upper earlier-noted length markings adjacent to upper tooth coronal crown end of rod 12. In that manner, length "L" of canal 2 of tooth 1 can be accurately measured.

It is further noted that other modifications may be made to the present invention, without departing from the scope of the invention, as noted, in the appended claims.

We claim:

1. An endodontic measuring kit, comprising:

a plurality of user selectable elongated cylindrical diameter measuring rods having graded diameters known to the user for insertion as probes into an endodontic canal wherein the diameter of the natural lower root tip aperture and length of the tooth canal from apical to coronal end are to be determined; and a plurality of user selectable elongated tapered rods having graded diameters;

said tapered rods each having a longitudinally extending portion having length measurement markings thereon for observing tooth depth from crown to lower root tip aperture;

said tapered rods having a tapered bottom end extending from said top cylindrical portion, a tapered bottom end having means for indicating contact made between said tapered bottom end and the natural contour of a lower endodontic root tip aperture whose diameter and whose length of the tooth canal from apical to coronal end are being determined.

2. The endodontic measuring kit as in claim 1 wherein said longitudinally extending portion is cylindrical.

3. The device of claim 1 wherein said tapered rod contact indicating means comprises pressure sensing means and visual indication means.

4. The device of claim 3 wherein said pressure sensitive means comprises a pressure sensitive coating upon said tapered bottom end, said coating developing a visual indication at the place of contact with the natural contour of the lower endodontic root tip aperture.

5. The device of claim 3 wherein said cylindrical rods and said tapered rods are flexible for arcuate determination of endodontic lower root tip aperture diameter and overall tooth depth from crown to said lower root tip aperture.

6. The device of claim 1 wherein said tapered rod contact indicating means comprises an electric circuit and electric pressure sensitive switch means capable of generating a signal variable according to the place of contact upon said tapered bottom end; and signal receiving and signal display means for visual display of the place upon said tapered bottom end at which contact has been made.

7. The device of claim 1, wherein said tapered rod contact indicating mean comprises a moldable material.

8. The device of claim 7 wherein said moldable material is heated gutta percha.

9. The device of claim 7 wherein said moldable material is a mixture of gutta percha and a solvent.

10. The device of claim 7 wherein said solvent is selected from the group consisting of chloroform, halothane and eucalyptol.

11. The device of claim 1 wherein said cylindrical measuring rods further include a rounded, domed leading edge.

12. In endodontic dentistry, a method of measuring the diameter of a lower endodontic root tip aperture and measuring overall tooth depth from crown to lower root tip, comprising the steps of:

a. into a tooth open at the crown, selecting and inserting as a probe a cylindrical diameter measuring rod of a small, known diameter into said tooth and through the natural lower root tip aperture;

b. removing the diameter measuring rod of small, known diameter and inserting a different cylindrical measuring rod having a known, incrementally larger diameter as a probe into said tooth and through the natural lower root tip aperture;

c. determining the diameter of the natural aperture of the lower tip of a selected tooth root by repeating step "b" above as necessary with successively larger diameter cylindrical measuring rods until a cylindrical measuring rod encounters contact resistance when the user attempts to insert it into the natural lower root tip aperture;

d. noting the diameter of the first cylindrical measuring rod that encounters contact resistance at the natural lower root tip aperture and then removing said measuring rod e. inserting into said root tip aperture a tapered-bottom cylindrical measuring rod wherein said tapered bottom-cylindrical rod has contact indicating means on said tapered-bottom and said tapered-bottom measuring rod has a known diameter matching that of the natural lower root tip aperture and, wherein said tapered-bottom measuring rod has length markings on its cylindrical portion;

f. determining the crown to lower root tip depth for the diameter-determined selected root tip by noting the length markings adjacent to the tooth crown on the tapered-bottom measuring rod when its tapered-bottom is in contact with the natural aperture of a selected lower root tip; and g. withdrawing said tapered-bottom measuring rod from the tooth for which depth is being determined;

h. observing and noting the place on said tapered bottom where said contact indicating means shows a visible contact indication; and i. measuring and noting the distance between said visible contact indication and the earlier-noted length markings adjacent to the tooth crown.

* * * * *